US00PP20391P2

(12) United States Plant Patent
Pieters

(10) Patent No.: US PP20,391 P2
(45) Date of Patent: Oct. 6, 2009

(54) ***CHRYSANTHEMUM* PLANT NAMED 'PPP DEST 07'**

(50) Latin Name: *Chrysanthemum morifolium*
Varietal Denomination: PPP DEST 07

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/218,776

(22) Filed: Jul. 18, 2008

(51) Int. Cl.
*A01H 5/00* (2006.01)

(52) U.S. Cl. ..... Plt./291
(58) Field of Classification Search ..... Plt./291, Plt./287, 292
See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by large, pale-pink decorative type inflorescences with a darker pink center, consistent flowering response to short days, blooming consistently after 49 days of short day length, free branching habit, and a consistent natural season flowering habit during the first week of September.

1 Drawing Sheet

Latin name of the genus and species: *Chrysanthemum morifolium.*

Variety denomination: 'PPP DEST 07'.

BACKGROUND OF THE INVENTION

The new cultivar 'PPP DEST 07' is a product of a cross between the male parent 'Yellow Ovaro' (U.S. Plant Pat. No. 6,581) and the female parent 'Paularo Lilac' (not patent in the United States). The new cultivar was discovered and selected by Dirk Pieters in September of 2001 in Oostnieuwkerke, Belgium.

Asexual reproduction of the new cultivar 'PPP DEST 07' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP DEST 07' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP DEST 07.' These characteristics in combination distinguish 'PPP DEST 07' as a new and distinct *Chrysanthemum cultivar:*

1. Large, light pink decorative-type inflorescences with a darker pink center;
2. Consistent flowering response to short days, blooming consistently after 49 days of short day length;
3. Free branching habit; and
4. Consistent natural season flowering habit during the first week of September.

Plants of the new cultivar 'PPP DEST 07' are similar to plants of the male parent variety, 'Ovaro Yellow' in most horticultural characteristics, however plants of the new cultivar 'PPP DEST 07' are taller and wider. Also, the new cultivar 'PPP DEST 07' has different color ray florets than the male parent. Finally, 'PPP DEST 07' naturally blooms two to three weeks earlier than the male parent 'Ovaro Yellow.'

Plants of the new cultivar 'PPP DEST 07' are similar to plants of the female parent variety, 'Paularo Lilac' in most horticultural characteristics, however plants of the new cultivar 'PPP DEST 07' are taller and wider. Also, the new cultivar 'PPP DEST 07' has a bigger inflorescence diameter and more inflorescences per lateral branch. Additionally, 'PPP DEST 07' has lighter pink ray florets compared to the darker purple ray florets of the female parent. Finally, 'PPP DEST 07' naturally blooms two weeks earlier than 'Paularo Lilac.'

In comparison to the commercially available variety 'GEDI ONE JAM' (U.S. Plant Pat. No. 13,891), 'PPP DEST 07' is shorter and has wider plant spread. Additionally, 'GEDI ONE JAM' has more ray florets per inflorescence and a much larger inflorescence diameter than the new variety 'PPP DEST 07'. Further, the new variety 'PPP DEST 07' blooms one week earlier and has longer inflorescence longevity than the comparable variety. Finally, the inflorescences of 'PPP DEST 07' have a dark pink center compared to the light pink inflorescences of 'GEDI ONE JAM'.

BRIEF DESCRIPTION OF THE PHOTOGRAPH

The accompanying photograph illustrates in full color a typical plant of 'PPP DEST 07' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP DEST 07' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP DEST 07.'
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 23.5 cm.
Plant spread: Approximately 37 cm.
Growth rate: Moderate.
Branching characteristics: Free Branching.
Length of lateral branches: Approximately 16 cm.
Number of leaves per lateral branch: Approximately 20.
Age of plant described: Approximately 138 days.

FOLIAGE

Leaf:
*Arrangement.*—Alternate single.
*Average length.*—Approximately 3.6 cm.
*Average width.*—Approximately 2.4 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1.8 cm.
*Color.*—Young foliage upper side: Near Yellow-Green 147A. Young foliage under side: Near Green 137C. Mature foliage upper side: Near Yellow-Green 147A. Mature foliage under side: Near Green 137A.
*Venation.*—Type: Palmately net. Venation color upper side: Near Green 137D. Venation color under side: Near Green 138C.
Petiole:
*Average length.*—Approximately 1.2 cm.
*Color.*—Near Green 138B.
*Diameter.*—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately first week in September.
*Number of inflorescences per lateral branch.*—Approximately 13.
*Inflorescence diameter.*—Approximately 4 cm.
*Inflorescence depth.*—Approximately 1.6 cm.
*Inflorescence longevity on plant.*—Approximately 28 to 34 days.
*Persistence.*—Persistent.
Ray florets:
*Appearance.*—Matte.
*Texture.*—Smooth.
*Average number of ray florets per inflorescence.*—125.
*Shape.*—Spoon.
*Aspect.*—Flat.
*Margin.*—Entire.
*Apex.*—Obtuse.
*Base.*—Fused along 50% of its length.
*Length.*—Approximately 1.8 cm.
*Width.*—Approximately 0.4 cm.
*Color.*—Upper surface at first opening: Near Red-Purple 59C. Upper surface at maturity: Near Red-Purple 62C. Upper surface at fading: Near Red-Purple 69D. Under surface at first opening: Near Red-Purple 58A. Under surface at maturity: Near Red-Purple 65C with lateral stripes of Purple 75C. Under surface at fading: Near Red-Purple 69D. Center ray florets: Near Red-Purple 60C.
Disc florets:
*Appearance.*—Matte.
*Texture.*—Smooth.
*Average number of florets per disc.*—Approximately 54.
*Shape.*—Cylindric.
*Apex.*—Obtuse.
*Average length.*—Approximately 0.3 cm.
*Average width.*—Approximately 0.1 cm.
*Color.*—At first opening: Near Yellow-Orange 13A. At maturity: Near Yellow-Orange 13A. At fading: Near Yellow-Orange 13C.
Peduncle:
*Length.*—At terminal end (shortest): Approximately 5.2 cm. At lateral end (longest): Approximately 7.7 cm.
*Angle to stem.*—Acute.
*Strength.*—Moderate.
*Color.*—Near Yellow-Green 147A.
*Habit.*—Upright.
*Diameter.*—Approximately 0.2 cm.
*Surface texture.*—Lightly pubescent.
Inflorescence bud:
*Length.*—Approximately 0.8 cm.
*Diameter.*—Approximately 0.5 cm.
*Form.*—Globular.
*Color.*—Near Red-Purple 63A.
Involucral bracts (phyllaries):
*Appearance.*—Matte.
*Texture.*—Lightly pubescent.
*Number.*—Approximately 25.
*Shape.*—Oblanceolate.
*Margin.*—Entire.
*Apex.*—Acute.
*Length.*—Approximately 0.6 cm.
*Width.*—Approximately 0.4 cm.
*Color.*—Upper side: Near Green 137A. Under side: Near Green 137C.

REPRODUCTIVE ORGANS

Ray florets:
*Number of pistils per floret.*—1.
*Stigma shape.*—2 branched.
*Stigma color.*—Near Yellow 7A.
*Style color.*—Near Green-Yellow 1C.
*Style length.*—Approximately 0.4 cm.
*Stamens.*—Absent.
Disc florets:
*Number of pistils per floret.*—1.
*Stigma shape.*—Cylindric.
*Stigma color.*—Near Yellow 7A.

*Style length.*—Approximately 0.3 cm.
*Style color.*—Near Yellow-Green 154C.
*Number of stamens per floret.*—Approximately 5.
*Anther shape.*—Tubular.
*Anther color.*—Near Yellow 7A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP DEST 07' as herein illustrated and described.

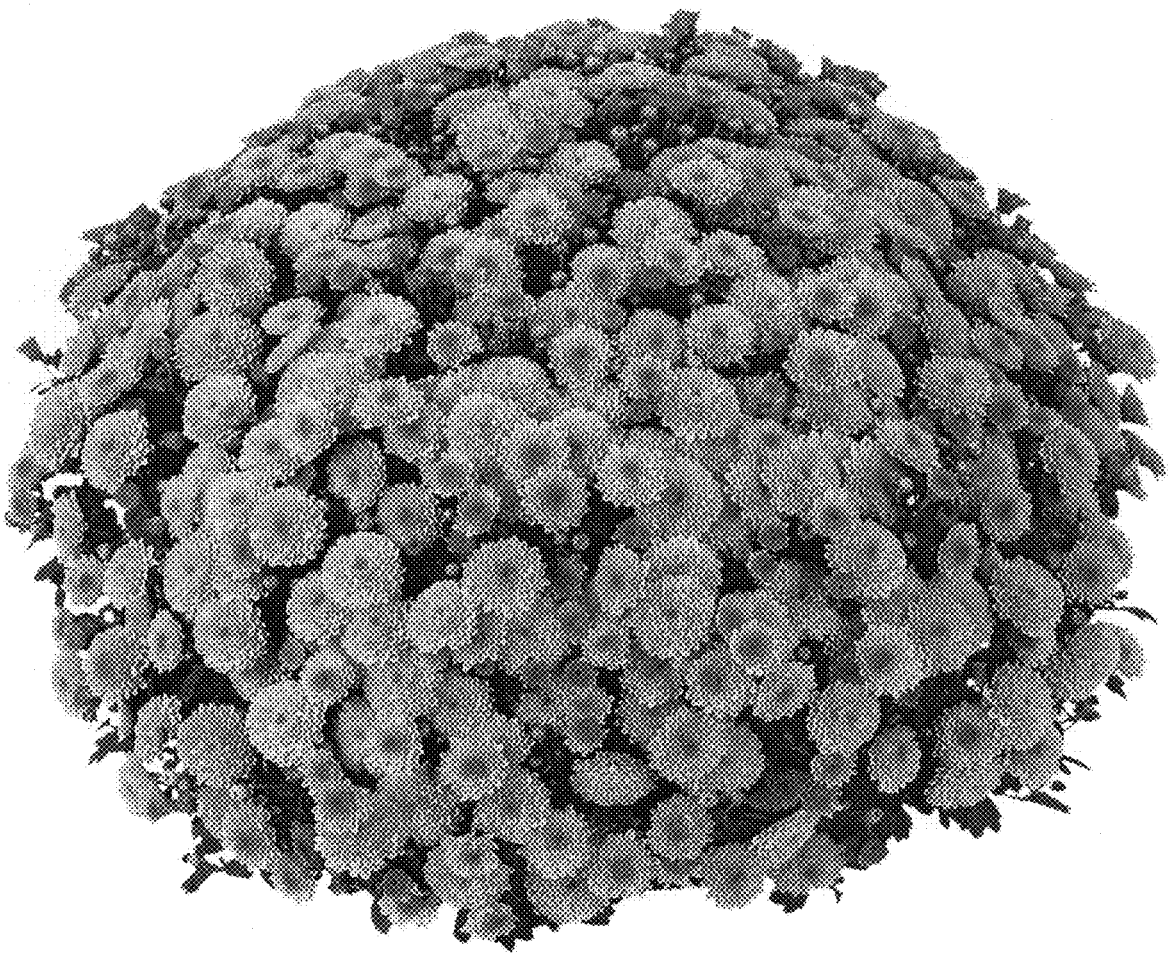

* * * * *